Figure 1:
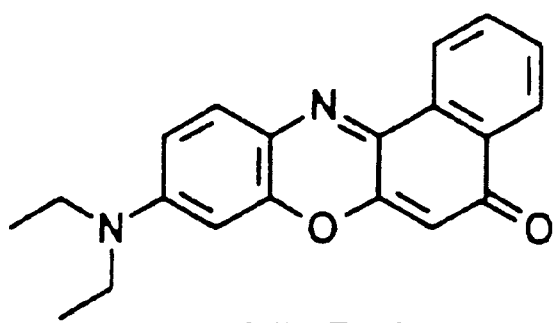
Figure 1:
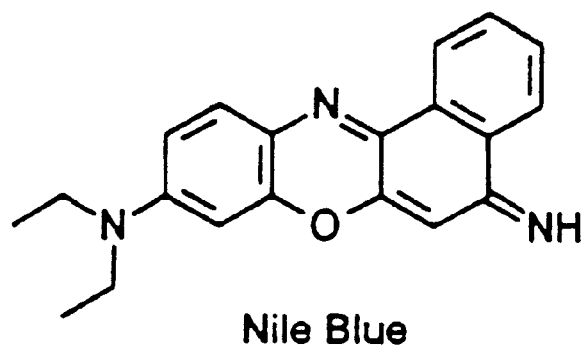
Figure 1:
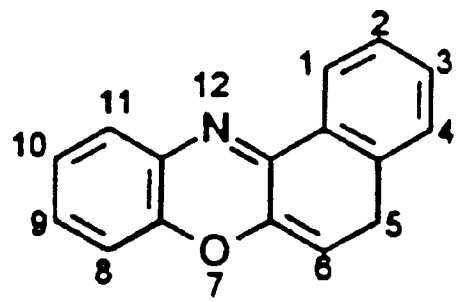
Figure 2A:
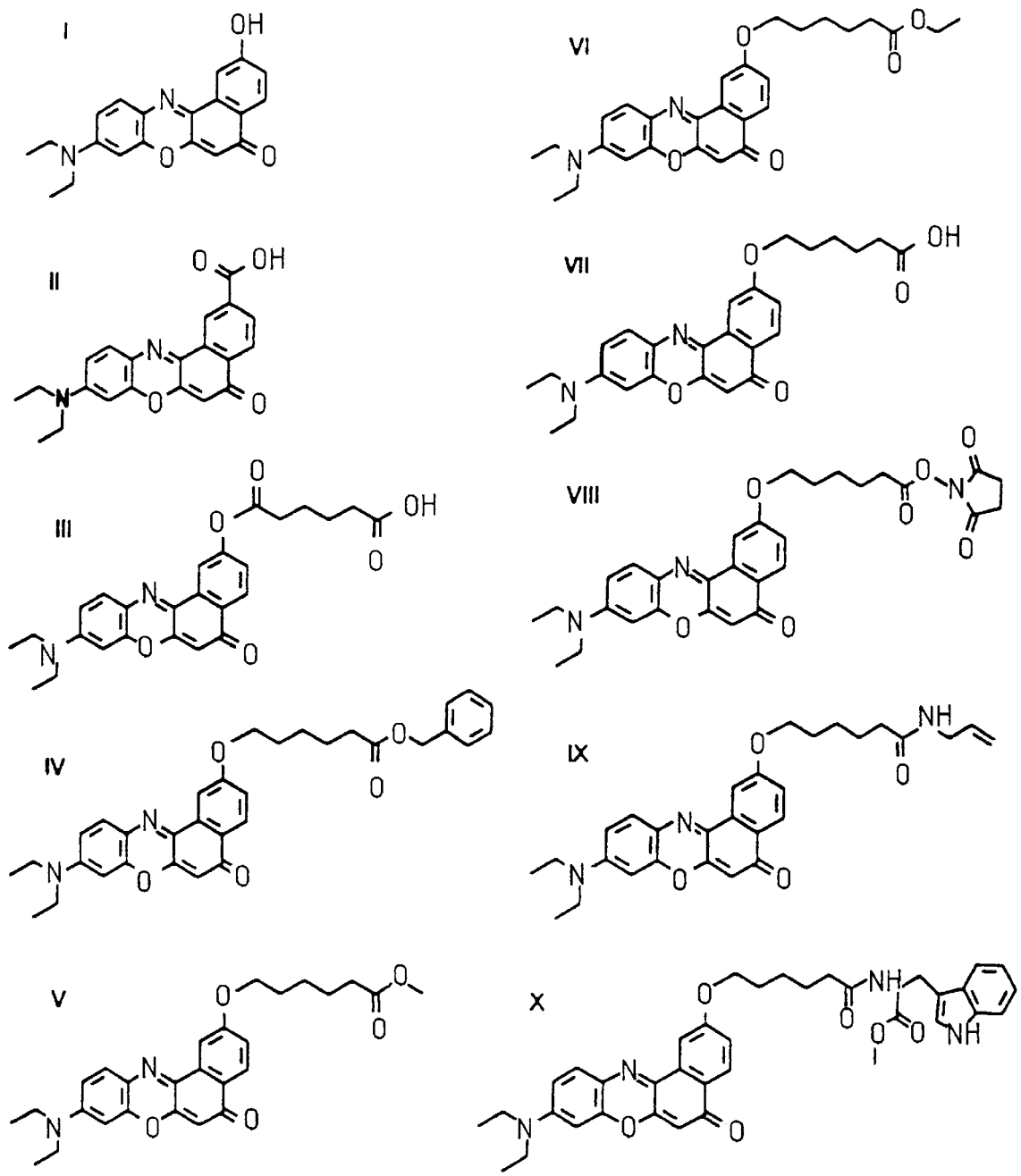
Figure 2B:
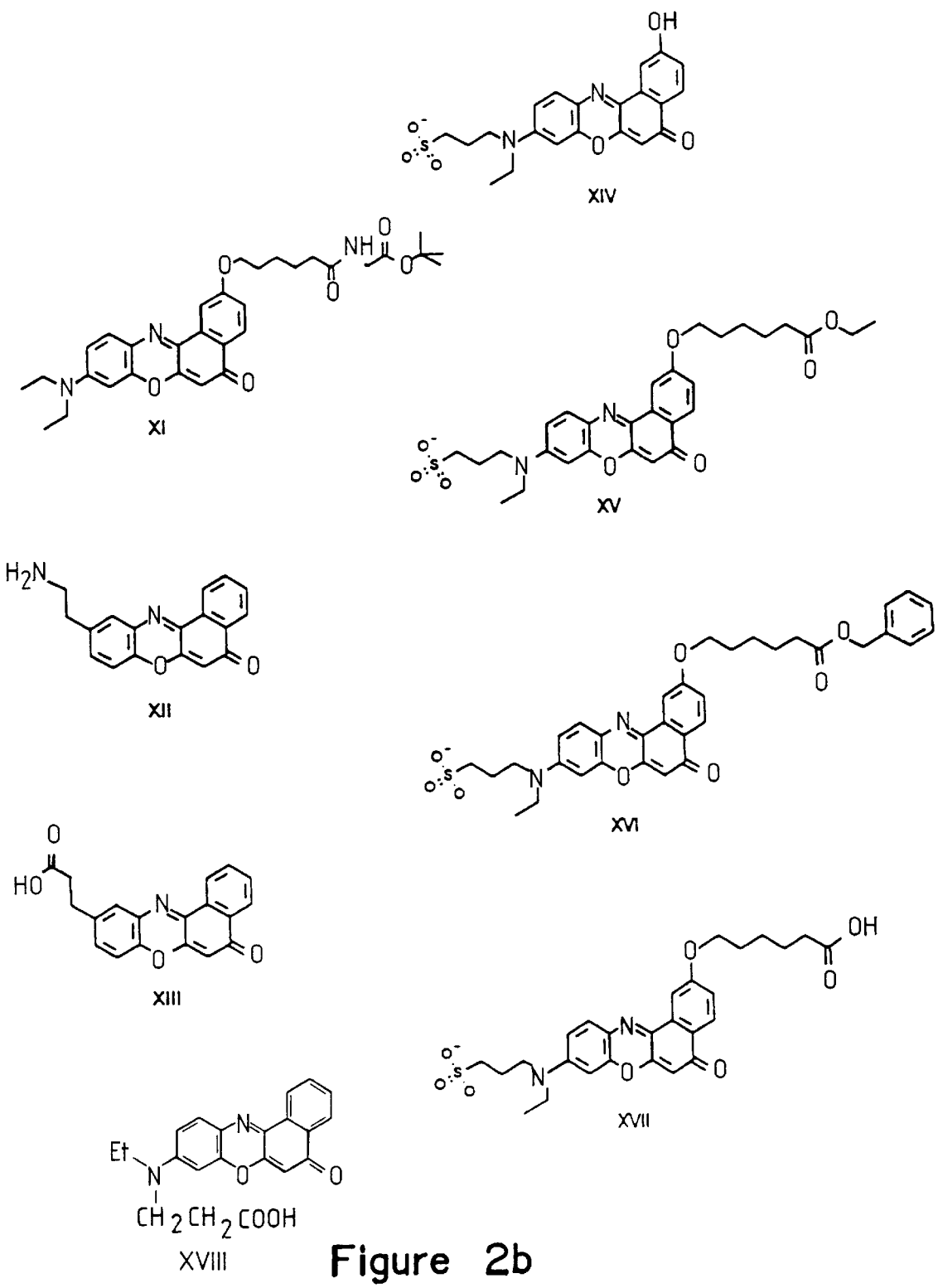

United States Patent

Simmonds et al.

[11] Patent Number: 6,166,202
[45] Date of Patent: Dec. 26, 2000

[54] BENZOPHENOXAZINE DYES

[75] Inventors: Adrian Simmonds, Bucks; James N Miller, Leics; Christopher John Moody, Exeter; Elizabeth Swann, Randalstown; Mark Samuel Jonathan Briggs, Amersham; Ian Edward Bruce, Dunslauglin, all of United Kingdom

[73] Assignee: Amersham Pharmacia Biotech UK Limited, Buckinghamshire, United Kingdom

[21] Appl. No.: 09/117,608
[22] PCT Filed: Feb. 5, 1997
[86] PCT No.: PCT/GB97/00324
  § 371 Date: Jan. 15, 1999
  § 102(e) Date: Jan. 15, 1999
[87] PCT Pub. No.: WO97/29154
  PCT Pub. Date: Aug. 14, 1997

[30] Foreign Application Priority Data

Feb. 5, 1996 [GB] United Kingdom .................. 9602265

[51] Int. Cl.[7] ...................... C07D 265/34; C07D 498/00; C07D 279/36; C07D 513/00; A01N 61/00
[52] U.S. Cl. .................................. 544/99; 544/1; 544/31; 514/1
[58] Field of Search .................................. 544/99, 1, 31; 514/1

[56] References Cited

U.S. PATENT DOCUMENTS

| | | | |
|---|---|---|---|
| 4,600,775 | 7/1986 | Theodoropulos | 544/99 |
| 4,962,197 | 10/1990 | Foley et al. | 544/31 |
| 5,283,330 | 2/1994 | Bhansali | 544/99 |

FOREIGN PATENT DOCUMENTS

| | | |
|---|---|---|
| 2 707 658 | 1/1995 | European Pat. Off. . |
| 0 747 447 | 12/1996 | European Pat. Off. . |
| 0 608 737 | 8/1994 | France . |

OTHER PUBLICATIONS

Alekseev, N.N. et al., "9–(dimethylamino)benzo(a)phenoxazin–5–one or its derivatives," *Chemical Abstracts*, 101(25):774 (Dec. 17, 1984) (Abstract 230551p).

Bhansali, K.G. et al., "Synthesis and Characterization of a Series of 5H–Benzo[a]–phenoxazin–5–one Derivatives as Potential Antiviral/Antitumor Agents," *Heterocycles*, 36(6):1239–1251 (1993).

Karnes, H.T. et al., "Long–Wavelength Derivatization Reagents for use in Diode Laser Induced Fluorescence Detection," *Proc. SPIE–Int. Soc. Opt. Eng.*, 2388:21–31 (1995).

Mank, A.J.G. et al., "Visible Diode Laser–Induced Fluorescence DEtection in Liquid Chromatography after Precolumn Derivation of Amines," *Analytical Chemistry*, 67(10):1742–1748 (May, 1995).

*The Chemistry of Synthetic Dyes*, Chapter 5, Part iiic, vol. 4, Venkataraman, Academic Press, New York, pp. 228–240 (1971).

*Primary Examiner*—Jezia Riley
*Attorney, Agent, or Firm*—Marshall, O'Toole, Gerstein, Murray & Borun

[57] ABSTRACT

Benzophenoxazine compounds have formula (I) where X is O or NH, Y is $NR^1R^2$ or H, $R^1$ and $R^2$ are alkyl or -L-A, L is a linker and A may be a reactive group by means of which the compound is linked to a biomolecule. The compounds can be used as fluorescent dyes for labelling biomolecules.

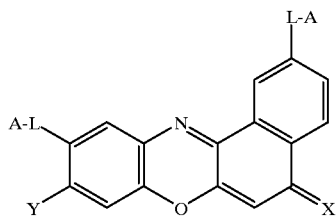

15 Claims, 5 Drawing Sheets

Nile Red

Nile Blue

Benzophenoxazine ring numbering scheme

Nile Red

Nile Blue

Benzophenoxazine ring numbering scheme

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: oligonucleotide primer
<221> NAME/KEY: misc_feature
<222> LOCATION: (1)
<223> OTHER INFORMATION: At position 1, N= C6-amino-link group

<400> SEQUENCE: 1
ntgtaaaacg acggccagt                                                19

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: synthetic peptide

<400> SEQUENCE: 2

Ala Tyr Val His Asp Ala Pro Val Arg Ser Leu Asn Lys
 1               5                  10

BENZOPHENOXAZINE DYES

Benzophenoxazine compounds provide a family of fluorescent dyes which can be used for labelling biological molecules in various applications. The phenoxazine dyes tend to have large Stokes' shifts of 80–100 nm. This is useful in simplifying the type of filtering needed to differentiate between excitation and emission wavelengths, and may enable sensitivity limits to be improved. The benzophenoxazines also appear to have particularly good photostability properties.

The benzophenoxazine dye Nile Red (9-diethylaminobenzo[a]phenoxazine-5-one) (FIG. 1) has been shown to be useful in the fluorescence detection of proteins. Binding of dye to protein has generally been accomplished through non-covalent, hydrophobic interactions. Fluorescence properties of the dye such as emission wavelength and intensity have been shown to be dependent on the polarity of the environment and this appears to be the reason for the different spectral properties on binding to different proteins. Its low fluorescence in water is thought to be due, at least in part, to the formation of dimers and higher aggregates, since there is a time-dependent decrease in intensity on addition of water.

In order to allow specific labelling of proteins and other biomolecules such as nucleic acids, attempts have been made to form covalent links, e.g. through the nitrogen at C5 on Nile Blue (5-amino-9-diethylaminobenzo[a]phenoxazine) (FIG. 1). Linkage to Nile Blue in this way, however, has been shown to be unsatisfactory because of the adverse effect this modification has on the dye's fluorescence properties (Mank et al., 1995. Anal. Chem., 67, 1742). Fluorescence quantum yield is reduced by a factor of 10 (from 27 to 2.50) and extinction coefficient is reduced by almost 20 times (from 75000 to 4000) (Karnes et al, 1995, Proc. SPIE-Int. Soc. Opt. Eng., 2388, 21).

Bhansali and Kook, Heterocycles, Volume 36, No 6, page 1239, 1993, describe the synthesis of benzophenoxazine compounds substituted at the 10 position for therapeutic applications by intercalating into DNA. It is also stated in U.S. Pat. No. 5,283,330 that the alanyl substituted compound can act as a protein dye. In neither of these cases was this class of compound covalently linked to the DNA or protein target, nor are the fluorescence properties of the compounds mentioned or described.

The benzophenoxazine ring numbering scheme is also shown in FIG. 1. This invention is concerned with novel derivatives of benzophenoxazines which have substituents at the 2 and/or 10 and/or the 9 position, which substituents do not cause a significant loss of fluorescence. Reactive groups at all three positions can be used for linkage to tracer molecules such as biomolecules or to introduce water solubilising functions in order to improve compatibility with aqueous systems or to change the fluorescence emission wavelength of the compound.

According to this invention there is provided a benzophenoxazine compound having the formula

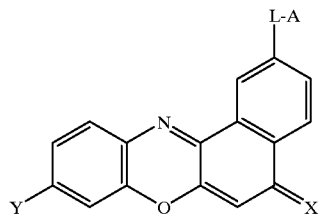

where

X is O or NH or N-alkyl or N-aryl or N-alkenyl,
Y is $NR^1R^2$ or H, $R^1$ and $R^2$ are the same or different and each is C1–C12 aryl, alkenyl or alkyl or is -L-A, in at least one -L-A:
   each L is a linker chain of 0–20 carbon atoms and which may contain one or more O or N or S atoms, and
   each A may be amine or amide or —CN or alcohol or thiol or carboxyl or sulfonate or phosphate, or a reactive group by means of which the benzophenoxazine compound may be covalently linked to a biomolecule or a group which enhances or reduces water solubility or provides electron donor or withdrawal properties to modify the spectral characteristics of the dye, and each other -L-A is H or C1–C20 alkyl.

In these compounds, the 5-substituent X may be O as in Nile Red or NH as in Nile Blue, or may be N-alkyl, N-aryl or N-alkenyl as in related dyes such as oxazine 170.

At the 9-position, each N-substituent $R^1$ and $R^2$ is the same or different C1–C12 alkyl or aryl or alkenyl or is -L-A.

In at least one -L-A group, L is a linker chain of 0 to 20 carbon atoms and which may include O or N or S atoms. Preferably the chain is at least three atoms in length, so as to avoid possible steric inhibition of reactions, e.g. —OC$_5$H$_{10}$— and —OCOC$_4$H$_8$— and —C$_2$H$_4$CO—.

The compound contains at least one group A which is an amine or amide or —CN or alcohol or thiol or carboxyl or sulfonate or phosphate or a reactive group by means of which the benzophenoxazine compound may be covalently linked to a biomolecule, or a group which enhances (e.g. polyether) or reduces (e.g. alkyl) water solubility or provides electron donor or withdrawal properties to modify the spectral characteristics of the dye, e.g. halogen, alkoxy, nitro or cyano. See The Chemistry of Synthetic Dyes, Venkataraman, Academic Press, N.Y. 1971, 4, Chapter 5 part iiic, p 228–240, particularly Table 1 on page 230. Preferred biomolecules are nucleosides, nucleotides and analogues thereof, oligonucleotides and nucleic acids, and also peptides, proteins, polysaccharides, lipids, sugars and other small molecules.

In another aspect, the invention provides a complex of a benzophenoxazine compound and a biomolecule, the benzophenoxazine compound having the formula

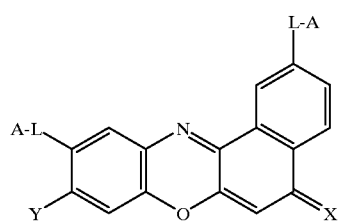

where X, Y, $R^1$, $R^2$, L and A are as defined above, and wherein the benzophenoxazine compound is covalently linked to the biomolecule through a reactive group A. These linkages can be conventional. For example, a carboxylate group A may be converted to a succinimide ester for reaction with an amine group of a nucleoside or nucleotide or peptide. Examples of other reactive groups most commonly used are isothiocyanate, iodoacetamides, sulphonyl chlorides, maleimides, phosphoramidites, phosphonates and azides. Preferably the linkage is through the 2-position, or through the 9-position or the 10-position of the benzophenoxazine molecule.

Any other group -L-A may optionally be hydrogen or C1–C20 alkyl.

EXPERIMENTAL

Commercially available solvents and reagents were used throughout without further purification, except for those detailed below which were purified as described. DMF was dried by stirring over calcium hydride for 15 h, decanted and distilled under reduced pressure before storage over molecular sieves under nitrogen. Methanol was distilled from magnesium turnings and iodine.

Analytical thin layer chromatography was carried out using aluminium-backed plates coated with Merck Kieselgel 60 $GF_{254}$. Plates were visualised under UV light (at 254 and/or 360 nm). Flash chromatography was carried out using Merck Kieselgel 60 H silica or Matrex silica 60. Pressure was applied at the column head with hand bellows. Samples were applied pre-adsorbed on silica. HPLC purification was carried out using either a C18 reverse phase column equilibrated in water with methanol elution or a PRP1 column equilibrated with 2% ammonia and using methanol elution.

IR spectra were recorded in the range 4000–600 $cm^{-1}$ using a Nicolet FT-205 spectrometer, with internal calibration. Spectra were recorded as KBr discs. UV/visible spectra were obtained using a Shimadzu UV-160 spectrophotometer. Uncorrected fluorescence spectra were recorded as dilute solutions on a Perkin Elmer LS50B luminescence spectrometer or a Hitachi F4500 using optiglass fluorescence cells. $^1H$ and $^{13}C$ NMR spectra were recorded on HPLC purified samples using Bruker AC-250, Bruker DPX400 and Bruker WH400 instruments (SERC NMR Spectroscopy Centre, Warwick, UK) and a Jeol GSX-270 instrument; J values were recorded in Hz. High and low-resolution mass spectra were recorded on a Kratos MS80 instrument or on a VG Analytical ZAB-E instrument (SERC Mass Spectrometry Service, Swansea). Melting points were measured on an Electrothermal digital melting point apparatus or on a Reichert-Kofler hot stage apparatus and are uncorrected.

EXAMPLE 1

Introduction of Functional Groups at the 2 Position

9-Diethylamino-2-hydroxy-5H-benzo[a]phenoxazin-5-one (I)

5-Diethylamino-2-nitrosophenol hydrochloride (1.14 g, 4.96+mmol) and 1,6-dihydroxynaphthalene (0.19 g, 4.94 mmol) were refluxed in DMF (100 ml) for 4 h. The DMF was removed under reduced pressure. The crude mixture was purified by flash chromatography (ethyl acetate—1:1 ethyl acetate:isopropanol elution), to yield a dark green crystalline solid.

Yield (1.1 g, 65%); m.p. >300° C.; (Found: $M^+$ 334.1317. $C_{20}H_{18}N_2O_3$ requires 334.1317); $v_{max}$ (KBr)/$cm^{-1}$ 3375, 2964, 1645, 1590, 1561; $\lambda_{max}$ (MeOH)/nm 547 ($\epsilon$30366), 326 (5762), 265 (27555), 210 (23380); $\delta_H$ (400 MHz; DMSO $d_6$) 10.42 (1H, broad s, OH), 7.96 (1H, d, J=8.6 Hz, 4–H), 7.87 (1H, d, J=2.4 Hz, 1–H), 7.55 (1H, d, J=9.0 Hz, 11–H), 7.08 (1H, dd, J=8.6 Hz, J=2.5 Hz. 3–H), 6.77 (1H, dd, J=9.0 Hz, J=2.5 Hz, 10–H), 6.61 (1H, d, J=2.5 Hz, 8–H), 6.13 (1H, s, 6–H), 3.48 (4H, q, J=7.0 Hz, N(C$\underline{H}_2$CH$_3$)$_2$), 1.15 (6H, t, J=7.0 Hz, N(CH$_2$C$\underline{H}_3$)$_2$); $\delta_C$ (100.6 MHz; DMSO $d_6$) 181.64 (CO), 160.69, 151.66, 150.74, 146.47, 138.77, 133.82, 130.88 (CH), 127.52 (CH), 123.92, 118.42 (CH), 109.96 (CH), 108.18 (CH), 104.15 (CH), 96.09 (CH), 44.48 ($\underline{C}H_2CH_3$), 12.52 (CH$_2\underline{C}$H3); m/z (EI) 335 (MH$^+$, 20%), 334 (M$^+$, 63), 320 (25), 319 (100), 291 (26); fluorescence in methanol strong.

9-Diethylamino-5-oxo-5H-benzo[a]phenoxazine-2-carboxylic Acid (II)

This was made similarly to the hydroxy derivative above except that the starting materials were 5-diethylamino-2-nitrosophenol hydrochloride and 1-hydroxynaphthalene-6-carboxylic acid.

EXAMPLE 2

Derivatisation of 2-Hydroxyl Analogue with a 6 Carbon Linker through Ester Formation 9-Diethylamino-5-oxo-5H-benzo[a]phenoxazin-2-yl (5-carboxy)pentanoate (III)

A mixture of the 9-diethylamino-2-hydroxy-5H-benzo[a]phenoxazin-5-one (0.096 g, 0.28 mmol), 1-cyclohexyl-3-(2-morpholinoethyl)carbodiimide metho-p-toluene sulfonate (0.18 g, 0.42 mmol), adipic acid (0.046 g, 0.31 mmol) and a catalytic quantity of 4-dimethylaminopyridine were stirred overnight in dichloromethane (30 ml). The crude mixture was washed with water, dried (Na$_2$SO$_4$) and concentrated. The residue was purified by column chromatography (ethyl acetate elution) to yield the acid as a dark red solid.

Yield (0.08 g, 60%); m.p. 85–87° C.; $v_{max}$ (film)/$cm^{-1}$ 3347, 3055, 2985, 2930, 1757, 1639, 1586; $\lambda_{max}$ (MeOH)/nm 558 ($\epsilon$22222), 267 (28090), 208 (17094); $\delta_H$ (250 MHz; CDCl$_3$) 8.32 (2H, 4–H, 1–H), 7.56 (1H, d, J=9.1 Hz, 11–H), 7.34 (1H, dd, J=8.7 Hz, J=2.3 Hz, 3–H), 6.62 (1H, dd, J=9.2 Hz, J=2.7 Hz, 10–H), 6.44 (1H, d, J=2.7 Hz, 8–H), 6.40 (1H, s, 6–H), 3.47 (4H, q, J=7.1 Hz, N(CH$_2$CH$_3$)$_2$), 2.68 (2H, t, J=7.0 Hz, COCH$_2$), 2.49 (2H, t, J=6.9 Hz, COCH$_2$), 1.26 (6H, t, J=7.1 Hz, N(CH$_2$CH$_3$)$_2$); $\delta_H$ (100.6 MHZ; CDCl$_3$) 182.91 (CO), 171.41 (CO), 153.18, 152.41, 151.05, 146.94, 139.05, 133.72, 131.30 (CH), 129.46, 127.66 (CH), 124.99, 123.48 (CH), 116.36 (CH), 109.93 (CH), 105.50 (CH), 96.39 (CH), 45.14 ($\underline{C}H_2CH_3$), 34.05 (CH$_2$), 29.70 (CH$_2$), 24.24 (CH$_2$), 24.14 (CH$_2$), 12.62 (CH$_2\underline{C}$H$_3$); m/z (Cl) 463 (MH$^+$, 84%), 335 (100), 146 (13), 74 (18) fluorescence in methanol strong.

EXAMPLE 3

Derivatisation of 2-Hydroxyl Analogue with a 6 Carbon Linker through Ether Formation Benzyl 6-(9-diethylamino-5-oxo-5H-benzo[a]phenoxazin-2-yloxy)hexanoate (IV)

A mixture of 9-diethylamino-2-hydroxy-5H-benzo[a]phenoxazin-5-one (0.1 g, 0.3 mmol), potassium carbonate (0.12 g, 0.9 mmol) and benzyl 6-bromohexanoate (0.11 g, 0.38 mmol) in DMF (50 ml) was refluxed for 4 h. Residual potassium carbonate was filtered off and the filtrate concentrated under reduced pressure. The crude residue was purified by column chromatography (petrol -petrol: ether, 1:1, 10% gradient elution) to yield a green crystalline solid.

m.p. 146–148° C.; (Found: M$^+$ 538.2470. $C_{33}H_{34}N_2O_5$ requires 538.2467); $v_{max}$ (KBr)/$cm^{-1}$ 2937, 2865, 1734, 1595; $\lambda_{max}$ (MeOH)/nm 551 ($\epsilon$27169), 267 (28144), 210 (30531); $\delta_H$ (250 MHz; CDCl$_3$) 8.20 (1H, d, J=8.7 Hz, 4–H), 8.02 (1H, d, J=2.5 Hz, 1–H), 7.59 (1H, d, J=9.1 Hz, 11–H), 7.35 (5H, broad s, Ph), 7.13 (1H, dd, J=8.7 Hz, J=2.6 Hz, 3–H), 6.63 (1H, dd, J=9.1 Hz, J=2.6 Hz, 10–H), 6.44 (1H, d, J=2.6 Hz, 8–H), 6.28 (1H, s, 6–H), 5.13 (2H, s, CH$_2$Ph), 4.14 (2H, t, J=6.2 Hz, ArOC$\underline{H}_2$), 3.45 (4H, q, J=7.0 Hz, N(C$\underline{H}_2$CH$_3$)$_2$), 2.43 (2H, t, J=7.3 Hz, C$\underline{H}_2$CO$_2$Bn), 1.85 (2H, m), 1.76 (2H, m), 1.58 (2H, m), 1.25 (6H, t, J=7.0 Hz, N(CH$_2$C H$_3$)$_2$); δ$_C$ (100.6 MHz; CDCl$_3$)184.14 (CO). 1173.34 (CO2Bn), 161.60, 151.90, 150.59, 146.67, 139.76, 133.95, 130.95 (CH), 128.50 (CH), 128.14 (CH), 127.56 (CH), 125.44, 124.57, 118.13 (CH), 109.40 (CH), 106.39 (CH), 105.10 (CH), 96.12 (CH), 67.93 (CH$_2$), 66.09 (CH$_2$), 44.97 (N(CH$_2$CH$_3$)$_2$), 34.14 (CH$_2$), 28.82 (CH$_2$), 25.59 (CH$_2$), 24.64 (CH$_2$), 12.57 (N(CH$_2$CH$_3$)$_2$); m/z (Cl) 539 (MH$^+$, 46%), 335 (22), 165 (22), 132 (100); fluorescence in methanol strong.

Methyl 6-(9-Diethylamino-5-oxo-5H-benzo[a]phenoxazin-2-yloxy)hexanoate (V)

This was formed by transesterification from the benzyl ester using the same procedure described for formation of the benzyl ester (IV) but using methanol as solvent.

m.p. 152–154° C.; ν$_{max}$ (KBr)/cm$^{-1}$ 2929, 2868, 1739, 1620, 1601, 1581; λ$_{max}$ (MeOH)/nm 553 (ε27800), 265 (27433), 212 (21459); δ$_H$ (400 MHz; CDCl$_3$) 8.19 (1H, d, J=8.7 Hz, 4-H), 8.01 (1H, d, J=2.6 Hz, 1-H), 7.57 (1H, d, J=9.0 Hz, 11-H), 7.13 (1H, dd, J=8.7 Hz, J=2.6 Hz, 3-H), 6.62 (1H, dd, J=9.1 Hz, J=2.7 Hz, 10-H), 6.42 (1H, d, J=2.7 Hz, H8), 6.26 (1H, s, 6-H), 4.16 (2H, t, J=6.4 Hz, ArOCH$_2$), 3.68 (3H, s, CO$_2$Me), 3.44 (4H, q, J=7.1 Hz, N(CH$_2$CH$_3$)$_2$), 2.38 (2H, t, J=7.4 Hz, CH$_2$CO$_2$Me), 1.88 (2H, m), 1.74 (2H, m), 1.58 (2H, m), 1.25 (6H, t, J=7.1 Hz, ν (CH$_2$CH$_3$)$_2$); δ$_C$ (100.6 MHz; CDCl$_3$) 183.51 (CO), 174.30 (CO), 152.30, 150.98, 147.09, 140.33, 134.33, 131.321, 128.83 (CH), 125.88 (CH), 124.95, 122.15, 117.61 (CH), 109.74 (CH), 106.88 (CH), 105.56 (CH), 96.58 (CH), 68.38 (CH$_2$), 51.78 (CO$_2$Me), 44.98 (CH$_2$), 34.26 (CH$_2$), 29.18 (CH$_2$), 25.97 (CH$_2$), 24.98 (NCH$_2$CH3), 12.90 (NCH$_2$CH$_3$); m/z (ES) 463 (MH$^+$, 28%), 234 (14), 194 (28), 179 (37), 98 (67), 84 (100); fluorescence in methanol strong.

Ethyl 6-(9-Diethylamino-5-oxo-5H-benzo[a]phenoxazin-2-yloxy)hexanoate (VI)

A mixture of 9-diethylamino-2-hydroxy-5H-benzo[a]phenoxazin-5-one (0.27 g, 0.81 mmol), potassium carbonate (0.34 g, 2.46 mmol) and ethyl 6-bromohexanoate (0.28 g, 1.26 mmol) in methanol (100 ml) was refluxed for 2 days. After this time full conversion was observed by TLC. Excess potassium carbonate was filtered off and the filtrate concentrated. The crude residue was evaporated and purified by column chromatography (ether elution), to yield a red crystalline solid.

Yield (0.21 g, 53%); m.p. 158–160° C.; (Found: M$^+$ 476.2311. C$_{28}$H$_{32}$N$_2$O$_5$ requires 476.2311); ν$_{max}$ (KBr)/cm$^{-1}$ 2927, 1735, 1628, 1600, 1582; λ$_{max}$ (MeOH)/nm 552 (ε44064), 267 (40664), 208 (38216); δ$_H$(250 MHz; CDCl$_3$) 8.21 (1H, d, J=8.7 Hz, 4-H), 8.04 (1H, d, J=2.6 Hz, 1-H), 7.60 (1H, d, J=9.1 Hz, 11-H), 7.15 (1H, dd, J=8.7 Hz, J=2.5 Hz, 3-H), 6.65 (1H, dd, J=9.1 Hz, J=2.7 Hz, 10-H). 6.45 (1H, d, J=2.7 Hz, 8-H), 6.29 (1H, s, 6-H), 4.15 (4H, m, CO$_2$CH$_2$CH$_3$, ArOCH$_2$), 3.47 (4H, q, J=7.1 Hz, N(CH$_2$CH$_3$)$_2$), 2.36 (2H, t, J=7.2 Hz, CH$_2$CO$_2$Et), 1.89 (2H, m), 1.75 (2H, m), 1.57 (2H, m), 1.26 (9H, t, J=7.1 Hz, N(CH$_2$CH$_3$)$_2$, CO$_2$CH$_2$CH$_3$); δ$_C$ (62.9 MHz; CDCl$_3$) 183.14 (CO), 173.86 (CO$_2$Et), 161.63, 151.92, 150.60, 146.69, 140.00, 133.95, 130.94 (CH), 127.57 (CH), 125.46, 124.57, 118.14, 109.39 (CH), 106.42 (CH), 105.13 (CH), 96.15 (CH), 67.95 (CH$_2$), 60.20 (CH$_2$), 44.97 (CH$_2$), 34.18 (CH$_2$), 28.84 (CH$_2$), 25.61 (CH$_2$), 24.65 (CH$_2$), 14.19 (CH$_3$), 12.55 (CH$_3$); m/z (EI) 477 (MH$^+$, 15%), 476 (M$^+$, 67), 461 (73), 431 (13), 291 (15), 233 (17); fluorescence in methanol strong.

6-(9-Diethylamino-5-oxo-5H-benzo[a]phenoxazin-2-yloxy)hexanoic Acid (VI)

The ethyl ester (ethyl 6-(9-diethylamino-5-oxo-5H-benzo[a]phenoxazin-2-yloxy)hexanoate) (0.055 g, 0.11 mmol) was suspended in ammonium dihydrogen phosphate (0.1 M, 5 ml, pH 7) and porcine liver esterase (0.6 ml, 1500 units) added. The mixture was stirred at 37° C. for 7 days and checked by TLC. The water was removed under reduced pressure. The residue was dissolved in methanol and the enzyme extract filtered off through celite. The crude mixture was purified by reverse phase chromatography (methanol elution), to yield a dark red crystalline solid.

Yield (0.032 g, 62%); m.p. 167–169° C.; (Found: MH$^+$ 449.2076. C$_{26}$H$_{28}$N$_2$O$_5$+H requires 449.2076); ν$_{max}$ (KBr)/cm$^{-1}$ 3435, 2953, 1653, 1638, 1619, 1593; λ$_{max}$ (MeOH)/nm 550 (ε30423), 325 (5824), 267 (28753), 210 (20759); δ$_H$ (250 MHz; MeOH d$_4$) 8.02 (1H, d, J=8.8 Hz, 4-H), 7.92 (1H, d, J=2.4 Hz, 1-H), 7.52 (1H, d, J=9.2 Hz, 11-H), 7.10 (1H, dd, J=8.8 Hz, J=2.5 Hz, 3-H), 6.76 (1H, dd, J=9.2 Hz, J=2.5 Hz, 10-H), 6.51 (1H, d, J=2.5 Hz, 8-H), 6.14 (1H, s, 6-H), 4.09 (2H, t, J=7.7 Hz, ArOCH$_2$), 3.49 (4H, q, J=7.1 Hz, N(CH$_2$CH$_3$)$_2$), 2.33 (2H, t, J=7.1 Hz, CH$_2$CO$_2$H), 1.86 (2H, m), 1.69 (2H, m), 1.56 (2H, m), 1.24 (6H, t, J=7.1 Hz, N(CH$_2$CH$_3$)$_2$); δ$_C$ (100.6 MHz; DMSO d$_6$) 181.49 (CO), 174.77 (CO$_2$H), 161.34, 151.78, 150.88, 146.54, 138.33, 133.64, 131.05 (CH), 127.30 (CH), 124.91, 124.00, 117.98 (CH), 110.12 (CH), 106.25 (CH), 104.14 (CH), 96.04 (CH), 67.95 (CH$_2$), 44.54 (CH$_2$), 34.01 (CH$_2$), 28.50 (CH$_2$), 25.26 (CH$_2$), 24.51 (CH$_2$), 12.57 (CH$_3$); m/z (FAB) 449 (MH$^+$, 54%), 330 (42), 308 (73), 290 (56), 165 (65); fluorescence in methanol strong.

EXAMPLE 4

Labelling of Model Biological Molecules

Synthesis of the Active Ester (Succinyl 6-(9-Diethylamino-5-oxo-5H-benzo[a]phenoxazin-2-yloxy)hexanoate) (VIII)

6-(9-Diethylamino-5-oxo-5H-benzo[a]phenoxazin-2-yloxy)hexanoic acid (0.12g, 0.26 mmol), 1-cyclohexyl-3-(2-morpholinoethyl)carbodiimide metho-p-toluenesulfonate (0.34 g, 0.8 mmol), N-hydroxysuccinimide (0.09 g, 0.8 mmol) and a catalytic quantity of 4-dimethylaminopyridine were stirred overnight in dichloromethane (25 ml). The solvent was removed under reduced pressure and the residue purified by column chromatography (ether) elution) to yield the active ester as a dark red solid.

Yield (0.13, 92%); m.p. 166–168° C.; (Found: M$^+$ 545.2160. C$_{30}$H$_{31}$N$_3$O$_7$ requires 545.2162); ν$_{max}$ (KBr)/cm$^{-1}$ 3400, 1737, 1623, 1617, 1589; λ$_{max}$ (MeOH/nm) 552 (ε30929), 325 (5359), 268 (27886), 210 (34608); δ$_H$ (250 MHz; CDCl$_3$) 8.20 (1H, d, J=8.7 Hz, 4-H), 8.02 (1H, d, J=2.5 Hz, 1-H) 7.58 (1H, d, J=9.2 Hz, 11-H), 7.15 (1H, dd, J=8.7 Hz, J=2.5 Hz, 3-H), 6.63 (1H, dd, J=9.2 Hz, J=2.7 Hz, 10-H), 6.43 (1H, d, J=2.7 Hz, 8-H), 6.28 (1H, s,6-H), 4.18 (2H, t, J=6.2 Hz, ArOCH$_2$), 3.45 (4H, q, J=7.1 Hz, N(CH$_2$CH$_3$)$_2$), 2.84 (4H, s, COCH$_2$CH$_2$CO), 2.68 (2H, t, J=7.2 Hz, CH$_2$CO$_2$N(COCH$_2$)$_2$),1.88 (4H, m), 1.68 (2H, m),1.25 (6H, t, J=7.1 Hz, N(CH$_2$CH$_3$)$_2$); δ$_C$ (100.6 MHz; CDCl$_3$) 169.46 (CO), 168.85 (CO), 162.09 (CO), 152.42, 151.10, 147.22, 140.50, 134.45 (CH), 131.44 (CH), 128.11, 126.03, 125.09, 118.68 (CH), 109.86 (CH), 107.02 (CH), 105.68 (CH), 96.72 (CH), 68.28 (CH$_2$), 45.42 (CH$_2$), 31.30 (CH$_2$), 29.12 (CH$_2$), 25.98 (CH$_2$),25.77 (CH$_2$), 24.78 (CH$_2$), 13.00 (N(CH$_2$CH$_3$)$_2$); m/z (EI) 546 (MH$^+$, 26%), 545 (M$^+$, 85), 530 (40), 430 (62), 415 (88), 262 (52), 233 (100); fluorescence in methanol strong.

Reaction of Active Ester with Allylamine (IX)

(a) Homogeneous reaction

To a stirred solution of the active ester VIII (0.039 g, 0.07 mmol) and a catalytic quantity of 4-dimethylaminopyridine in dichloromethane was added dropwise allylamine (0.026 ml, 0.35 mmol).

The mixture was stirred overnight. The solvent was removed under reduced pressure and the residue purified by column chromatography (ethyl acetate elution) to yield the allyl amide as a dark red solid (0.02 g, 59%).

(b) Biphasic Reaction

To a stirred solution of the active ester (0.06 g, 0.11 mmol) in dichloromethane (15 ml) was added a solution of sodium hydrogen carbonate (0.1 m, 8 ml) and sodium carbonate (0.1M, 8 ml) containing allyl amine (0.04 ml, 0.54 mmol) and tetrabutylammonium hydrogen sulfate (0.037 g, 0.11 mmol). The mixture was stirred for 2 h and followed by TLC. The layers were separated and the dichloromethane layer was dried ($MgSO_4$) and concentrated to yield the allylamide as a dark red solid (0.37 g, 69%).

6-(9-Diethylamino-5oxo-5H-benzo[a]phenoxazin-2-yloxy)hexanoic Acid Tryptophan Methyl Ester Amide (X)

A solution of the active ester VIII (0.035 g, 0.06 mmol), L-tryptophan methyl ester hydrochloride (0.049 g, 0.19 mmol) and pyridine (0.015 g, 0.19 mmol) in dichloromethane (20 ml) was stirred overnight. The solvent was removed under reduced pressure and the residue purified by column chromatography (ethyl acetate elution) to yield the trytophan amide as a dark red crystalline solid.

Yield (0.027 g, 65%); m.p. 75–77° C.; $v_{max}$ (KBr)/cm$^{-1}$ 3421, 3300, 2930, 1750, 1735, 1654, 1617, 1594, 1572; $v_{max}$ (MeOH)/nm 551 (ε38033), 326 (7308), 268 (42555), 220 (70697); $\delta_H$ (250 MHz; CDCl$_3$) 8.54 (1H, broad s, NH), 8.18 (1H, d, J=8.7 Hz, 4–H), 8.00 (1H, J=2.5 Hz, 1–H), 7.58 (1H, d, J=9.1 Hz, 11–H), 7.56 (1H, m), 7.36 (1H, m), 7.16 (4H, m), 6.61 (1H, dd, J=9.1 Hz, J=2.7 Hz, 10–H), 6.43 (1H, d, J=2.6 Hz, 8–H), 6.28 (1H, s, 6–H), 6.05 (1H, d, J=7.8 Hz, CONH), 4.97 (1H, td, J=7.8 Hz, J=5.6 Hz, HNC$\underline{H}$CO$_2$Me), 4.04 (2H, t, J=6.4 Hz, ArCH$_2$), 3.71 (3H, s, OMe), 3.45 (4H, q, J=7.1 Hz, N(C$\underline{H}_2$CH$_3$)$_2$), 3.32 (2H, t, J=5.6 Hz, CH(CO$_2$Me)C$\underline{H}_2$), 2.22 (2H, t, J=7.4 Hz, CH$_2$CON), 1.81. (2H, m), 1.72 (2H, m), 1.63 (2H, m), 1.25 (6H, t, J=7.1 z, N(CH$_2$C$\underline{H}_3$)$_2$); $\delta_C$ (100.6 MHz; CDCl$_3$) 183.67 (CO), 172.93 (CONH), 162.15 (CO$_2$Me), 152.46, 151.16, 147.22, 140.35, 136.59, 134.41, 131.38 (CH), 128.12 (CH), 125.92, 125.92, 125.10, 123.18 (CH), 122.60 (CH), 120.01 (CH), 119.88, 119.12, 118.86 (CH), 118.70 (CH), 111.79 (CH), 110.40, 109.97 (CH), 106.94 (CH), 105.61 (CH), 96.70 (CH), 68.42 (CH$_2$), 53.28 ($\underline{C}$HCO$_2$CH$_3$), 52.70 (CO$_2$Me), 45.43 (N$\underline{C}$H$_2$CH$_3$), 36.78 (CH$_2$), 29.23 (CH$_2$), 28.00 (CH$_2$), 25.92 (CH$_2$), 25.52 (CH$_2$), 13.00 (N(CH$_2\underline{C}$H$_3$)$_2$); m/z (ES) 649 (MH$^+$, 68%), 489 (9), 348 (23), 263 (100); fluorescence in methanol strong.

6-(9-Diethylamino-5-oxo-5H-benzo[a]phenoxazin-2-yloxy)hexanoic Acid Glycine Tert-Butyl Ester Amide (XI)

A mixture of 6-(9-diethylamino-5-oxo-5H-benzo[a] phenoxazin-2-yloxy)hexanoic acid (10 mg, 22 mmol), 1-(3-dimethylaminopropyl)-3-ethylcarbodiimide methiodide (ETC) (14 mg, 45 mmol) and N-hydroxysulfosuccinimide sodium salt (15 mg, 67 mmol) in DMF (1 ml) was stirred at room temperature. After 2.5 h a further portion of ETC (50 mg, 168 mmol) was added. The mixture was stirred at room temperature overnight and a solution of tert-butyl glycine hydrochloride (19 mg, 112 mmol) in pH 9.2 buffer (NaHCO$_3$/Na$_2$CO$_3$) (1.5 ml) was added dropwise. After 3 h the mixture was concentrated in vacuo and purified by flash column chromatography (C18, 50% methanol/water to 80% methanol/water gradient) to afford the title compound as a dark red solid (11 mg, 88%).

$d_H$ (270 MHz; CDCl$_3$) 8.21 (1H, d, J=8.8 Hz, 4–H), 8.03 (1H, d, J=2.5 Hz, 1–H), 7.61 (1H, d, J=9.1 Hz, 11–H), 7.15 (1H, dd, J=8.6 Hz and 2.6 Hz, 3–H), 6.65 (1H, dd, J=9.3 Hz and 2.7 Hz, 10–H), 6.45 (1H, d, J=2.8 Hz, 8–H), 6.29 (1H, s, 6–H ) 6.00 (1H, br t, J=5.2 Hz, NH), 4.17 (2H, t, J=6.3 Hz, ArOCH$_2$), 3.95 (2H, d, J=5.2 Hz, NHCH$_2$), 3.47 (4H, q, J=7.1 Hz, N(CH$_2$CH$_3$)$_2$), 2.30 (2H, d, J=7.4 Hz, CH$_2$CON), 1.95–1.68 (4H, m), 1.68–1.50 (2H, m), 1.47 (9H, s, Bu$^t$) and 1.26 (2H, t, J=7 Hz, N(CH$_2$CH$_3$)$_2$) fluorescence in methanol strong.

EXAMPLE 5

Derivatisation at the 10 Position with Alkylcarboxy or Alkylamino Groups 10-(2-Aminoethyl)-5H-benzo[a]phenoxazin-5-one (XII)

This was synthesised according to the methods of Bhansali and Kook (Petrocycles, 36, 1239–51, 1993).

10-(2-Carboxyethyl)-5H-benzo[a]phenoxazin-5-one (XIII)

This was synthesised according to the methods of Bhansali and Kook (1993) but using 3-(4-hydroxyphenyl) propionic acid as the phenolic substrate.

EXAMPLE 6

Introduction of Water-Solubilising Functionality into the Dialkylamino Grouping at the 9 Position 9(N-Ethyl-(N-3-sulfonylpropyl))amino-2-hydroxy-5H-benzo[a]phenoxazin-5-one (XIV)

3-(N-Ethyl-3-hydroxy4-nitrosoanilino)-propanesulfonic acid hydrochloride (0.53 g, 1.6 mmol) and 1,6-dihydroxynaphthalene (0.26 g, 1.6 mmol) were refluxed in DMF (40 ml) for 4 h. The DMF was removed under reduced pressure. The crude mixture was purified by flash chromatography (ethyl acetate-1:1 ethyl acetate: methanol, 10% gradient elution) to yield a dark green crystalline solid.

Yield (0.54 g, 79%); m.p. 147–149° C.; $v_{max}$ (KBr)/cm$^{-1}$ 3421, 2970, 1639, 1617, 1592, 1560; $\lambda_{max}$ (MeOH)/nm 547 (ε28969), 326 (5541), 264 (26761), 212 (21805); $\delta_H$ (400 MHz; MeOH d$_4$) 7.92 (1H, d, J=8.6 Hz, 4–H), 7.76 (1H, d, J=2.4 Hz, 1–H), 7.35 (1H, d, J=9.1 Hz, 11–H), 6.98 (1H, dd, J=8.6 Hz, J=2.5 Hz, 3–H), 6.68 (1H, dd, J=9.1 Hz, J=2.5 Hz, 10–H), 6.41 (1H, d, J=2.5 Hz, 8–H), 6.03 (1H, s, 6–H), 3.53 (2H, t, J=7.7 Hz, HO$_3$SCH$_2$CH$_2$C$\underline{H}_2$N), 3.46 (2H, q, J=7.0 Hz, CH$_3$C$\underline{H}_2$N), 2.91 (2H, t, J=7.2 Hz, HO$_3$SC$\underline{H}_2$), 2.11 (2H, m, HO$_3$SCH$_2$C$\underline{H}_2$CH$_2$N), 1.22 (3H, t, J=7.0 Hz, C$\underline{H}_3$CH$_2$N); $\delta_C$ (100 MHz; MeOH d$_4$) 182.91 (CO), 160.09, 151.65, 150.80, 145.82, 137.56, 133.52, 130.15 (CH), 126.49 (CH), 124.24, 123.14, 117.02 (CH), 109.73 (CH), 107.60 (CH), 102.64 (CH), 95.28 (CH), 48.47 (CH$_2$), 47.67 (CH$_2$), 44.40 (CH$_2$), 22.21 (CH$_2$), 10.69 (CH$_3$); m/z (ES) 428 (M$^-$, 23%), 427 (M–H$^-$, 100); fluorescence in methanol strong.

Ethyl 6-(9(N-ethyl-(N-3-sulfonylpropyl))amino-5-oxo-5H-benzo[a]phenoxazin-2-yloxy)hexanoate (XV)

A mixture of 9(N-ethyl-(N-3-sulfonylpropyl))amino-2-hydroxy-5H-benzo[a]phenoxazin-5-one (0.34 g, 0.86 mmol), potassium carbonate (0.56 g, 4.06 mmol) and ethyl 6-bromohexanoate (0.95 g, 4.26 mmol) in DMF (25 ml) was refluxed overnight. Excess potassium carbonate was filtered off and the filtrate concentrated. The crude residue was purified by column chromatography (ethyl acetate—1:1 ethyl acetate:methanol, 10% gradient elution) to yield a red crystalline solid.

Yield (0.4 g, 87%); m.p. 150–152° C.; $v_{max}$ (KBr)/cm$^{-1}$ 3442, 2928, 2869, 1733, 1619, 1596; $\lambda_{max}$ (MeOH)/nm 552 (E 20732), 326 (3963), 266 (19539), 212 (14886); $\delta_H$ (400 MHz; MeOH d$_4$) 7.93 (1H, d, J=8.6 Hz, 4–H), 7.81 (1H, d, J=2.5 Hz, 1–H), 7.44 (1H, d, J=9.1 Hz, 11–H), 7.00 (1H, dd, J=8.7 Hz, J=2.5 Hz, 3–H), 6.76 (1H, dd, J=9.3 Hz, J=2.5 Hz, 10–H), 6.50 (1H,, d, J=2.5 Hz, 8–H), 6.05 (1H, s, 6–H), 4.04 (4H, m, ArOCH$_2$, CO$_2$CH$_2$CH$_3$), 3.50 (4H, m, HO$_3$SCH$_2$CH$_2$CH$_2$N, NCH$_2$CH$_3$), 2.82 (2H, t, J=7.2 Hz, HO$_3$SCH$_2$CH$_2$CH$_2$N), 2.29 (2H, t, J=7.3 Hz, CH$_2$CO$_2$Et), 2.03 (2H, m, HO$_3$SCH$_2$CH$_2$CH$_2$N), 1.77 (2H, m), 1.62 (2H, m), 1.47 (2H, m), 1.16 (6H, m, NCH$_2$CH$_3$, CO$_2$CH$_2$CH$_3$); $\delta_C$ (100.6 MHz; MeOH d$_4$) 184.18 (CO), 174.70 (CO$_2$Et), 162.54, 153.12, 152.29, 147.35, 138.87, 134.64, 131.58 (CH), 127.60 (CH), 125.55, 125.35, 118.41 (CH), 111.20 (CH), 106.65 (CH), 96.67 (CH). 68.50 (CH$_2$), 60.66 (CH$_2$), 49.26 (CH$_2$), 45.72 (CH$_2$), 34.26 (CH$_2$), 29.14 (CH$_2$), 25.03 (CH$_2$), 23.44 (CH$_2$), 13.78 (CH$_3$), 11.94 (CH$_3$); m/z (ES) 570 (M$^-$, 39%), 569 (M–H$^-$, 100); fluorescence in methanol strong.

Benzyl 6-(9-(N-ethyl-(N-3-sulfonylpropyl))amino-5-oxo-5H-benzo[a]phenoxazin-2-yloxy)hexanoate (XVI)

A mixture of 9(N-ethyl-(N-3-sulfonylpropyl))amino-2-hydroxy-5H-benzo[a]phenoxazin-5-one (0.54 g, 1.26 mmol), potassium carbonate (0.52 g, 3.76 mmol) and benzyl 6-bromohexanoate (0.47 g, 1.65 mmol) in DMF (25 ml) was refluxed overnight. Excess potassium carbonate was filtered off and the filtrate concentrated.. The crude residue was purified by column chromatography (ethyl acetate—1:1 ethyl acetate:methanol, 10% gradient elution) to yield a red crystalline solid.

Yield (0.4 g, 51%); m.p. 156–158° C.; $v_{max}$ (KBr)/cm$^{-1}$ 3448, 2938, 1735, 1640, 1619, 1595; $\lambda_{max}$ (MeOH)/nm 551 ($\epsilon$7973), 326 (1546), 267 (7535), 209 (7496); $\delta_H$(400 MHz; MeOH d$_4$) 7.98 (1H, d, J=8.7 Hz, 4–H), 7.83 20 (1H, d, J=2.4 Hz, 1–H), 7.48 (1H, d, J=9.1 Hz, 11–H), 7.30 (5H, m, Ph), 7.03 (1H, dd, J=8.8 Hz, J=2.5 Hz, 3–H), 6.80 (1H, dd, J=9.1 Hz, J=2.6 Hz, 10–H), 6.54 (1H, d, J=2.6 Hz, 8–H), 6.10 (1H, s, 6–H), 5.12 (2H, s, CH$_2$Ph), 4.03 (2H, t, J=6.4 Hz, ArOCH$_2$), 3.54 (2H, t, J=7.7 Hz, HO$_3$SCH$_2$CH$_2$CH$_2$N), 3.51 (2H, q, J=7.1 Hz, NCH$_2$CH$_3$), 2.91 (2H, t, J=7.2 Hz, HO$_3$SCH$_2$), 2.44 (2H, t, J=7.3 Hz, CH$_2$OBn), 2.14 (2H, m, HO$_3$CH$_2$CH$_2$CH$_2$N), 1.80 (2H, m), 1.74 (2H, m), 1.52 (2H, m), 1.25 (3H, t, J=7.1 Hz, NCH$_2$CH$_3$); $\delta_C$ (100.6 MHz; MeOH d$_4$) 184.97 (CO), 175.1 9 (CO$_2$Bn), 163.28, 153.85, 153.08, 148.11, 139.66, 137.73, 135.39, 132.37, 129.58 (CH), 129.23 (CH), 128.40 (CH), 126.35, 119.20 (CH), 111.98 (CH), 107.47 (CH), 97.48 (CH), 69.28 (CH$_2$), 67.23 (CH$_2$), 46.54 (CH$_2$), 35.07 (CH$_2$), 26.65 (CH$_2$), 25.90 (CH$_2$), 25.87 (CH$_2$), 24.30 (CH$_2$), 12.80 (CH$_3$); m/z (ES) 633 (MH$^+$, 17%), 632 (M$^+$, 43), 281 (30), 255 (49), 177 (60), 130 (68), 100 (100); fluorescence in methanol strong.

6-(9-N-Ethyl-(3-sulfonylpropyl)amino-5-oxo-5H-benzo[a]phenoxazin-2-yloxy)hexanoic acid (XVII)

Ethyl 6-(9(N-ethyl-(N-3-sulfonylpropyl))amino-5-oxo-5H-benzo[a]phenoxazin-2-yloxy)hexanoate (0.3 g, 0.55 mmol) was dissolved in ammonium dihydrogen phosphate (0.1 M, 50 ml. pH 7) and porcine liver esterase (6.3 ml, 20000 units) added. The mixture was stirred at 37° C. for 14 days. The water was removed under reduced pressure. The residue was dissolved in methanol and the enzyme extract filtered off through celite. The crude mixture was purified by reverse phase chromatography on preadsorbed silica (methanol elution), to yield a dark red crystalline solid.

Yield (0.15 g, 53%); m.p. 222–225° C.; $v_{max}$ (KBr)/cm$^{-1}$ 3441, 3064, 2934, 1732, 1640, 1619, 1594; $\lambda_{max}$ (MeOH)/nm 557 ($\epsilon$28648), 531 (31100), 325 (6233), 261 (28726), 216 (21551); $\delta_H$ (250 MHz; MeOH d$_4$) 7.74 (1H, d, J=8.8 Hz, 4–H), 7.49 (1H, d, J=2.3 Hz, 1–H), 7.22 (1H, d, J=9.1 Hz, 11–H), 6.82 (1H, dd, J=8.7 Hz, J=2.5 Hz, 3–H), 6.65 (1H, dd, J=9.1 Hz, J=2.3 Hz, 10–H), 6.31 (1H, d, J=2.3 Hz, 8–H), 5.86 (1H, S, 6–H), 3.89 (2H, t, J=6.2 Hz, ArOCH$_2$), 3.50 (4H, m, HO$_3$SCH$_2$CH$_2$CH$_2$N, NCH$_2$CH$_3$), 7.10 (2H, t, J=7.1 Hz, HO$_3$SCH$_2$), 2.37 (2H, t, J=7.2 Hz, CH$_2$CO$_2$H), 2.10 (2H, m, HO$_3$SCH$_2$CH$_2$CH$_2$N), 1.77 (4H, m), 1.50 (2H, m), 1.22 (3H, t, J=7.0 Hz, NCH$_2$CH$_3$); $\delta_C$ (100.6 MHz; MeOH d$_4$) 185.21 (CO), 177.96 (CO$_2$H), 163.71, 154.21, 153.57, 139.93, 135.77, 132.84 (CH), 128.77 (CH), 126.89, 126.47, 119.65 (CH), 112.52 (CH), 107.79 (CH), 105.32 (CH), 97.92 (CH), 69.78 (CH$_2$), 51.10 (CH$_2$), 49.07 (CH$_2$), 47.03 (CH$_2$), 35.41 (CH$_2$), 30.49 (CH$_2$), 27.24 (CH$_2$), 26.39 (CH$_2$), 24.79 (CH$_2$), 13.28 (NCH$_2$CH$_3$); m/z (ES) 542 (M$^+$, 22%), 255 (14), 177 (100); fluorescence in methanol strong.

EXAMPLE 7

Fluorescence Characterisation of Derivatised Molecules

Effect on Fluoresence of Derivatisation and Linkage of Benzophenoxazines to Biological Molecules Fluorescence spectra (uncorrected) were determined on 1 $\mu$M methanol solutions of HPLC purified samples using a Hitachi F4500 spectrofluorimeter. Relative fluorescence was determined from the emission curve at the peak excitation wavelength using the "area" function on the fluorimeter.

| | Excitation peak (nm) | Emission peak (nm) | Relative peak fluorescence |
|---|---|---|---|
| Nile Red | 558 | 635 | 1 |
| VII | 558 | 633 | 0.70 |
| XI | 558 | 633 | 0.72 |
| XVII | 558 | 633 | 0.73 |

The data clearly show that modification at the 2 and the 9 position resulted in only a small decrease in fluorescence intensity compared to the that of the parent compound.

Relative Fluorescence in Aqueous Environment of Nile Red and a Derivative Containing Water Solubilising Functions Spectra were determined 1 hour after diluting 100 $\mu$M methanolic solutions 100 fold into 50 mM Tris buffer pH 7.1. Relative fluorescence was determined from the emission curve at the peak excitation wavelength using the "area" function on the fluorimeter.

The results showed a time dependent decrease in fluorescence of Nile Red in buffer. After 1 hour there was a 33 fold difference in Nile Red fluorescence intensity in methanol compared to that in water (see table). This was associated with a large light scatter peak at the excitation wavelength, presumably due to aggregation of the fluorophore. Compound XVII, which has a sulfonic acid group to provide water solubilising properties, showed a fluorescence in water which was reduced by only 3.6 fold compared to its fluorescence in methanol. The intensity appeared not to vary with time.

|  | Peak excitation and emission in methanol (nm) | Relative fluorescence in methanol* | Peak excitation and emission in buffer (nm) | Relative fluorescence in buffer* |
|---|---|---|---|---|
| Nile Red | 558/635 | 1.00 | 599/657 | 0.03 |
| XVII | 558/633 | 0.73 | 592/651 | 0.20 |

*Relative to the fluorescence intensity of Nile Red in methanol.

Figure 3:
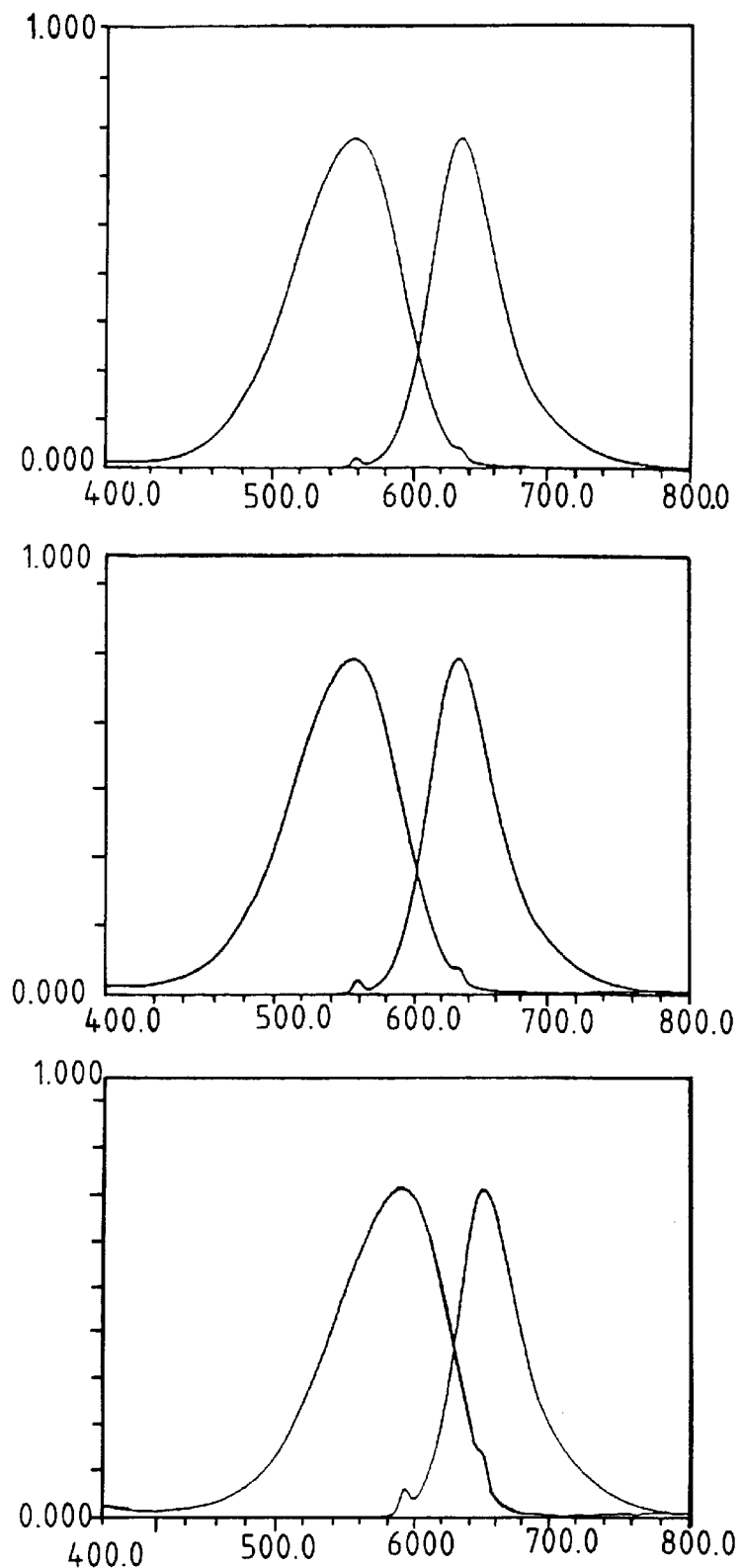

Normalised spectra of Nile Red and compound XI in methanol, and compound XVII in buffer are shown in FIG. 3.

EXAMPLE 8

Synthesis of 9-(N-2-carboxyethyl-N-ethyl)amino-5H-benzo[a]phenoxazin-5-one (XVIII)

Synthesis of N-(2-methoxycarbonyl)ethyl-N-ethyl-m-aminophenol

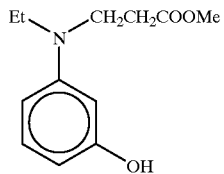

Step 1
Synthesis of N-ethyl-m-aminophenol from resorcinol
Resorcinol (200 g, 1.82 mol) was heated to 140–150° C. and stirred. Monoethylamine* was steadily passed through the melt for 32 hours. The viscous oily product was stirred and washed with hot water (3×200 ml) to remove unreacted resorcinol.
* This was provided by heating a solution of 70% monoethylamine in water.
The mono-ethylated product was purified by vacuum distillation (bp 159–162° C. at 8 mm Hg).
GC-MS analysis confirms the product to be pure with very little starting material and impurities present.
Yield=103.65 g, m/z (GC-MS) 137 ($M^+$).
Step 2
Reaction with methyl acrylate
N-Ethyl-m-aminophenol (48 g, 0.035 mol), methyl acrylate (100 ml) and acetic acid (150 ml) were heated under reflux for 4 hours, after which time tlc analysis (silica; dichloromethane-acetone 95:5) confirmed the completion of the reaction. The excess methyl acrylate/acetic acid was removed under vacuum at a temperature no greater than 70° C. The residual oil was then neutralised with NaOH solution, extracted with DCM and isolated.
Yield=45 g; m/z (GC-MS) 223 (M+), 208 ($M^+$-Me), 150 (M+—$CH_2CO_2Me$).

Synthesis of Dye (XVIII) Methyl Ester Derivative

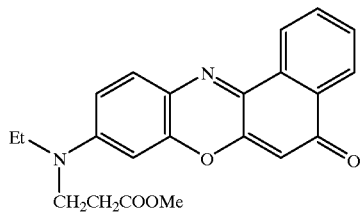

N-Ethyl-m-aminophenol (4g, 0.0179 mol) was dissolved in water (6 ml) and conc. HCl (10 ml) and heated to 60° C., stirring vigorously. The solution was cooled to −5° C. and a solution of sodium nitrite (10 ml) added over 10 minutes (the solution was made up by mixing 5 ml of a saturated solution of NaCl in water with 5 ml containing 1.5 g sodium nitrite (0.022 moles)). Another 5 ml of saturated NaCl solution was added and the solution stirred at 0° C. for 1 hour. The supernatant liquid was decanted off and the oily nitroso product used directly in the next stage.

The nitroso derivative was dissolved in ethanol (40 ml) to which 1-naphthol (3.0 g, 0.021 moles) was added. This solution was heated under reflux for 20 hours after which a distinct colour change from yellow/brown to violet had occurred.

The dye methyl ester was isolated by column chromatography (silica/dichloromethane plus 5% acetone) and dried in a vacuum dessicator.

Yield=1.0 g, 15%; m/z (FAB) 377 ($MH^+$), 399 ($MNa^+$).

Hydrolysis to Give Dye (XVIII)

The methyl ester (0.5 g) was stirred in water (50 ml) and conc. HCl (15 ml) at 80–90° C. for 3 hours.

The solution was neutralised to pH 5 with 30% NaOH and the solid product filtered off and dried in a vacuum dessicator.

Yield=0.34 g; purity by tlc satisfactory; UV $\lambda_{max}$ (MeOH) 552 nm, $\lambda_{emission}$ (562 nm excitation) (MeOH) 636 nm.; (10 mM HEPES pH 8.1) $\lambda_{emission}$ (590 nm excitation) (10 mM HEPES pH 8.1) 661 nm; $\delta_H$ (300 MHz; DMSO-$d_6$) 1.13 (3H, t, J7.0 Hz, Me), 2.57 (2H, t, J 7.0 Hz, $CH_2CO_2H$), 3.51 (2H, br. q, $CH_2Me$), 3.68 (2H, t, J 7.0 Hz, $CH_2CH_2$), 6.29 (1H, s, 6–CH), 6.68 (1H, d, J 2.6 Hz, 8–CH), 6.83 (1H, dd, J 9.2 and 2.6 Hz, 10–CH), 7.62 (1H, d, J 9.2 Hz, 11–CH), 7.71 and 7.81 (each 1H, m, 2 and 3–CH), 8.11 and 8.54 (each 1H, d, J8.1 Hz, 1 and 4–CH) ppm m/z (MALDI TOF) 362 ($M^+$).

EXAMPLE 9

Labelling of Oligonucleotides with Dye (VII)

Figure 4:
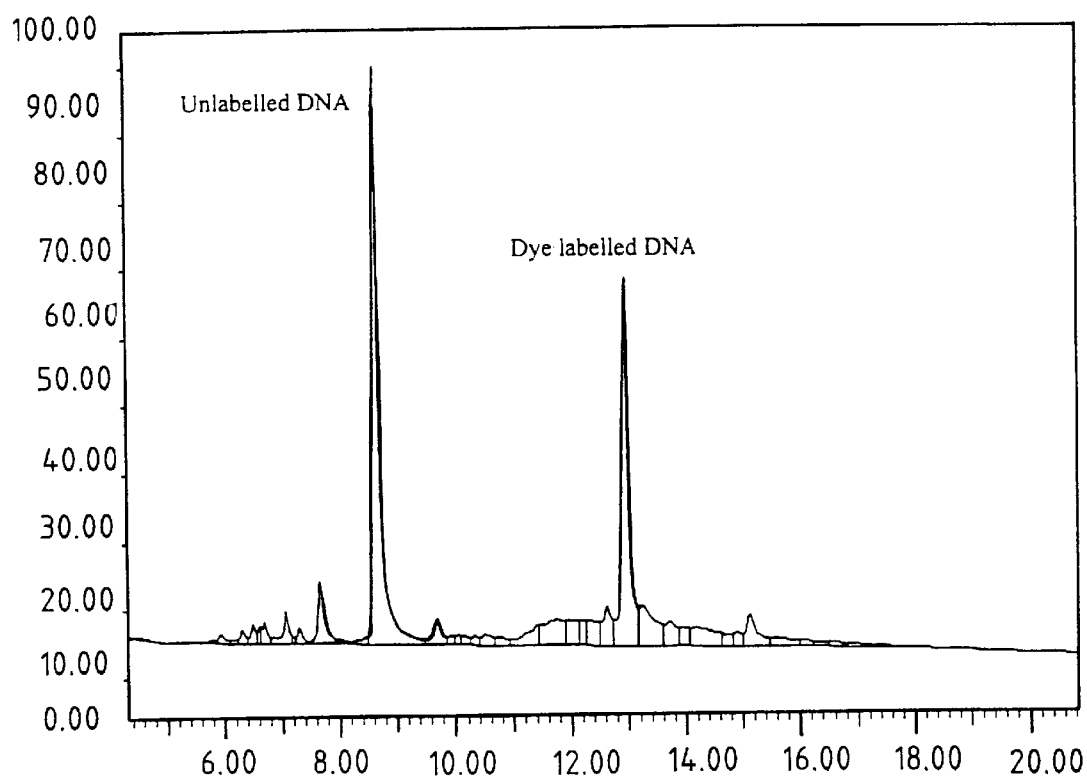

The DNA sequence $T_6$ was synthesised on an ABI 381A DNA synthesiser using standard reagents and cycles. The final monomer added to the 5' terminus of the resin bound oligomer was C6 aminolink (Glen Research) then the trityl protecting group was removed under standard conditions. The dye (VII) (8.6 mg, 100 eq.) was dissolved in DCM (0.2 ml) then diisopropylethylamine (3.5 µl, 100 eq.) was added followed by HBTU (7.5 mg, 100 eq.). The solution was then added to the DNA synthesis column by double syringe methodology, i.e. two syringes attached to either side of the DNA synthesis column were used to repeatedly pass the reaction mixture through the column, for 2 h. Then the column was washed with DCM (2×20 ml). The resin bound DNA was then cleaved from the solid support by treatment of the resin with $K_2CO_3$/MeOH (10% w/v) for 1 h., all volatiles were then removed in vacuo, and the product was isolated by reverse phase HPLC (DYNAMAX C18) using the following eluant system (FIG. 4).

Buffer A=0.1M Triethylammonium acetate
Buffer B=0.1M Triethylammonium acetate/MeCN (50/50 v/v)

| Time/min. | Flow rate/ml/min. | % Buffer B |
|---|---|---|
| 0 | 4 | 0 |
| 3 | 4 | 0 |
| 4 | 4 | 10 |
| 25 | 4 | 100 |
| 27 | 4 | 100 |
| 28 | 4 | 0 |

The isolated product was characterised by MALDI TOF MS m/z 2373.2 [$C_{92}H_{114}N_{15}O_{47}P_6$ requires 2373.8] and UV $\lambda_{max}$ ($H_2O$) 260 and 600 nm.

Similarly the oligonucleotide primer 5'-C6-amino-link-tgtaaaacgacggccagt-3' (SEQ. ID. NO.:1) was labelled using the dye NHS ester (VIII) using a solution chemistry approach.

A mixture of the amino-linked primer (10 OD units) and dye NHS ester (VIII) (0.5 mg) in DMF (60 µl) and 0.2M carbonate buffer (55 µl) was incubated for 16 hours at room temperature. The oligonucleotide was then ethanol precipitated twice and redissolved in 5% aqueous acetonitrile to give the required labelled oligonucleotide along with some unlabelled material. UV $\lambda_{max}$ 260 and 598 nm

EXAMPLE 10

Synthesis of a Range of Dye Labelled Peptide NH₂-AYVHDAPVRSLNK-OH (SEQ. ID. NO.:2)

The peptide is a substrate for Interleukin Converting Enzyme (ICE) which cleaves the peptide between the DA residues.

The peptide was synthesised on a Applied Biosystems model 431A peptide synthesiser using standard Fmoc chemistry. At the end of the synthesis the N-terminal Fmoc group was removed, however the protected peptide was left attached to the solid support, in which form it was reacted with the N-hydroxysuccinimidyl ester of dyes (I),(XVII) and (XVIII). The labelled peptide was then cleaved from the solid support using standard techniques and then purified by reverse phase HPLC.

Synthesis of N-hydroxysuccinimidyl ester of dye (XVII)

Dye (XVII) (4 mg, 7.4 µg), N-hydroxysuccinimide (5 mg, 44 µg), N-cyclohexyl-N'-(2-morpholinoethyl)-carbodiimide methyl p-toluene sulphonate (9.3 mg, 22 µg), 4-dimethylaminopyridine (catalytic amount—one small crystal) were placed in a round bottomed flask to which was added 1 ml of dry DMF. The mixture was stirred magnetically overnight (18 hrs) with light excluded at 22° C.

Labelling of the peptide 32 mg of the ICE substrate peptide (equivalent to 8 µm peptide) was weighed into a 1.5 ml screw top polypropylene V-vial to which was added the NHS reaction mixture followed by 20 µl of diisopropylethylamine. The vial was placed on rollers with light excluded for 20 hrs at ambient temperature (22° C.). The resin was then filtered off using a sintered glass frit, washed with 5 ml dry DMF, 5 ml methanol and finally 5 ml dichloromethane then dried in vacuo for 2 hrs.

Cleavage of the labelled peptide from solid support

The resin was placed in a small round bottomed flask to which was added 2 ml of an ice-cold solution of trifluoroacetic acid (1.8 ml), water (50 µl), ethanedithiol (50 µl) and thioanisole (100 µl). The mixture was stirred magnetically for 90 minutes and allowed to warm to ambient temperature. The mixture was then filtered through a glass wool plug and allowed to drip into 10 ml of ice cold diethyl ether. The dark blue precipitate was spun down, the supernatant removed, the precipitate redissolved in 1 ml trifluoroacetic acid and reprecipitated in 10 ml ice cold ether. The precipitate was spun down, washed twice with ether then dried in vacuo.

HPLC purification

The crude labelled peptide was dissolved in 1 ml water, filtered through a 0.45 µm Millipore filter and purified on a semi-prep. C-18 Vydac column (code 218TP510) using a gradient of 0.1% TFA/water to 70% of 0.1% TFA/acetonitrile over 20 minutes and a flow of 4 ml/minute. Detection was at 230 nm.

Two major peaks were eluted, the first at 10.5 minutes was colourless, the second at 13.5 minutes was blue. This second peak was freeze dried to give 2.3 mg (1.15 µm) of a bright blue solid. Mass spectroscopy of this material gave a single peak at 1995 m.u. (calculated molecular wt. of dye (XVII) labelled peptide=1991.3)

The following dyes were also used to label the above manner using analogous procedures Dye (II)

Dye (II) (3 mg) gave, after purification and freeze drying, 1 mg (0.6 µm) of the labelled peptide as a bright blue solid. Mass spectroscopy of this material gave a single peak at 1820 m.u. (calculated molecular wt. of dye (II) labelled peptide 1812.7)

Dye (XVIII)

Dye (XVIII) gave, after purification and freeze drying, 6 mg (3.3 µm) of the labelled peptide as a bright blue solid. Mass spectroscopy of this material gave a single peak at 1816 m.u. (calculated molecular wt. of dye (XVIII) labelled peptide=1812.7)

What is claimed is:

1. A benzophenoxazine compound having the formula

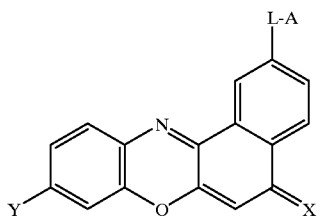

where
X is O or NH or N-alkyl or N-aryl or N-alkenyl,
Y is —NR$^1$R$^2$ or H,
R$^1$ and R$^2$ are the same or different and each is C1–C12 aryl, alkenyl or alkyl or is -L-A,
in at least one -L-A:
L is a linker chain of 0–20 carbon atoms and which may contain one or more O or N or S atoms, and
A may be amine or amide or —CN or alcohol or thiol or carboxyl or sulfonate or phosphate, or a reactive group by means of which the benzophenoxazine compound may be covalently linked to a biomolecule, or a group which enhances water solubility or provides electron donor or withdrawal properties to modify the spectral characteristics of the dye,
with the proviso that when L is zero, then A is not H, and each other -L-A is H or C1–C20 alkyl.

2. A compound as claimed in claim 1 wherein the benzophenoxazine ring 2-substituent L is —OC$_n$H$_{2n}$— or —OCOC$_n$H$_{2n}$— where n is 1 to 20.

3. A compound as claimed in claim 1, wherein in the benzophenoxazine ring 2-substituent L is —OC$_5$H$_{10}$— or —OCOC$_4$H$_8$—.

4. A compound as claimed in claim 2, wherein the -L-A-group at the benzophenoxazine ring 2 position is —OC$_n$H$_{2n}$COOH wherein n is 1 to 20.

5. A compound as claimed in claim 2, wherein the -L-A-group at the benzophenoxazine ring 2 position is —OC$_5$H$_{10}$COOH.

6. A compound as claimed in claim 1, wherein at least one group R$^1$ or R$^2$ is —C$_n$H$_{2n}$SO$_3$H where n is 1–12.

7. 6-(9-N-Ethyl-(3-sulfonylpropyl)amino-5-oxo-5H-benzo[a]phenoxazin-2-yloxy) hexanoic acid.

8. A compound as claimed in claim 1, wherein R$^1$ is —C$_n$H$_{2n}$COOH where n is 1–12.

9. 9-(N-2-carboxyethyl-N-ethyl)amino-5H-benzo[a]phenoxazin-5-one.

10. A complex of a biomolecule with a benzophenoxazine compound having the formula

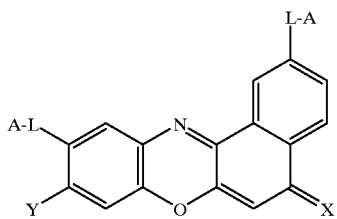

where
X is O or NH or N-alkyl or N-aryl or N-alkenyl,
Y is —NR$^1$R$^2$ or H,
R$^1$ and R$^2$ are the same or different and each is C1–C12 aryl, alkenyl or alkyl or is -L-A,
in at least one -L-A:
L is a linker chain of 0–20 carbon atoms and which may contain one or more O or N or S atoms, and A may be amine or amide or —CN or alcohol or thiol or carboxyl or sulfonate or phosphate, or a reactive group by means of which the benzophenoxazine compound may be covalently linked to a biomolecule, or a group which enhances water solubility or provides electron donor or withdrawal properties to modify the spectral characteristics of the dye, with the proviso that when L is zero, then A is not H, and each other -L-A is H or C1–C20 alkyl.

11. A complex as claimed in claim 1, wherein the biomolecule is a nucleoside or nucleotide or analogue thereof, or an aligonucleotide or nucleic acid.

12. A complex as claimed in claim 10, wherein the biomolecule is a nucleoside or nucleotide or analogue thereof, or an oligonucleotide or nucleic acid.

13. A complex as claimed in claim 10, wherein the biomolecule is a protein, peptide or amino acid.

14. A complex as claimed in claim 10, wherein the biomolecule is a polysaccharide, oligosaccharide or monosaccharide.

15. A complex as claimed in claim 10, wherein the biomolecule is a drug or a small molecule.

* * * * *

UNITED STATES PATENT AND TRADEMARK OFFICE
CERTIFICATE OF CORRECTION

PATENT NO. : 6,166,202
DATED : December 26, 2000
INVENTOR(S) : Simmonds et al.

It is certified that error appears in the above-identified patent and that said Letters Patent is hereby corrected as shown below:

Column 17,
Line 13, "aligonucleotide" should be -- oligonucleotide --.

Signed and Sealed this

Twenty-first Day of August, 2001

Attest:

*Attesting Officer*

NICHOLAS P. GODICI
*Acting Director of the United States Patent and Trademark Office*